(12) United States Patent
Diebold et al.

(10) Patent No.: US 8,076,267 B2
(45) Date of Patent: Dec. 13, 2011

(54) ENHANCERS FOR WATER SOLUBLE SELECTIVE AUXIN TYPE HERBICIDES

(75) Inventors: R. Shane Diebold, Victoria (CA); Kim F. Morgan, Shawnigan Lake (CA); Cameron D. Wilson, Victoria (CA)

(73) Assignee: W. Neudorff GmbH KG, Emmerthal (DE)

( * ) Notice: Subject to any disclaimer, the term of this patent is extended or adjusted under 35 U.S.C. 154(b) by 1239 days.

(21) Appl. No.: 11/686,098

(22) Filed: Mar. 14, 2007

(65) Prior Publication Data

US 2007/0197386 A1    Aug. 23, 2007

Related U.S. Application Data

(63) Continuation-in-part of application No. 11/252,192, filed on Oct. 17, 2005, now abandoned, which is a continuation of application No. 10/374,643, filed on Feb. 26, 2003, now Pat. No. 6,972,273.

(51) Int. Cl.
*A01N 43/40* (2006.01)
*A01N 25/00* (2006.01)

(52) U.S. Cl. .................. 504/116.1; 504/130

(58) Field of Classification Search .............. 504/116.1, 504/130
See application file for complete search history.

(56) References Cited

U.S. PATENT DOCUMENTS

| | | | |
|---|---|---|---|
| 4,808,207 A * | 2/1989 | Gotlieb et al. ............... 504/117 |
| 5,500,130 A | 3/1996 | Smith et al. |
| 5,520,818 A | 5/1996 | Smith et al. |
| 5,585,005 A | 12/1996 | Smith et al. |
| 5,656,571 A | 8/1997 | Miller et al. |
| 5,668,082 A | 9/1997 | Miller et al. |
| 6,107,246 A | 8/2000 | Prescott et al. |
| 6,117,823 A | 9/2000 | Smiley |
| 6,258,749 B1 | 7/2001 | Nonomura |
| 6,258,750 B1 | 7/2001 | Simpson et al. |
| 6,271,177 B1 | 8/2001 | Hudetz et al. |
| 6,323,153 B1 | 11/2001 | Smiley |
| 6,383,985 B1 | 5/2002 | Sedun et al. |
| 6,426,093 B1 | 7/2002 | Chevion et al. |
| 6,444,614 B2 | 9/2002 | Dean |
| 6,455,472 B1 | 9/2002 | Fischer et al. |
| 6,541,422 B2 | 4/2003 | Scher et al. |
| 6,589,912 B2 | 7/2003 | Kawai et al. |
| 6,608,003 B2 | 8/2003 | Smiley |
| 6,706,666 B2 | 3/2004 | Hasebe et al. |
| 6,972,273 B2 | 12/2005 | Sedun et al. |
| 2002/0016491 A1 | 2/2002 | Scher et al. |
| 2003/0087764 A1 * | 5/2003 | Pallas et al. .................. 504/365 |
| 2006/0084575 A1 | 4/2006 | Sedun et al. |

FOREIGN PATENT DOCUMENTS

| | | |
|---|---|---|
| DE | 260646 | 10/1988 |
| DE | 295077 A5 | 10/1991 |
| JP | 58162508 | 9/1983 |
| JP | 7215806 | 8/1995 |
| WO | 9702747 | 1/1997 |
| WO | 9938382 | 8/1999 |
| WO | 0003599 | 1/2000 |
| WO | 01/44236 A1 | 6/2001 |
| WO | 0150862 | 7/2001 |

OTHER PUBLICATIONS

Chemindustry.com chemical information for L-Ethylenediaminedisuccinic acid; http://www.neis.com/chemicals/1482985.html.
International Search Report issued for PCT/EP03/02/69, completed Jul. 17, 2003. (3 pages).

* cited by examiner

*Primary Examiner* — Sabiha Qazi
(74) *Attorney, Agent, or Firm* — Nutter McClennen & Fish LLP

(57) ABSTRACT

An improved selective herbicide, as well of methods of controlling unwanted plants using such a herbicide, are provided. A method for treating undesired vegetation can include providing a selective herbicidal composition that includes a water-soluble selective auxin-type herbicide and a chelating agent complexed with at least one transition metal, and contacting vegetation with a herbicidally effective amount of the composition such that unwanted vegetation is controlled, while desired vegetation is unaffected.

19 Claims, No Drawings

ENHANCERS FOR WATER SOLUBLE SELECTIVE AUXIN TYPE HERBICIDES

CROSS-REFERENCE TO RELATED APPLICATIONS

This application is a continuation-in-part of U.S. patent application Ser. No. 11/252,192, filed on Oct. 17, 2005, entitled "Composition and Method for Selective Herbicide," which is a continuation of U.S. patent application Ser. No. 10/374,643, filed on Feb. 26, 2003, now U.S. Pat. No. 6,972,273 and entitled "Composition and Method for Selective Herbicide," which claims priority to U.S. Provisional Patent Application No. 60/361,217, filed on Mar. 1, 2002, all of which are expressly incorporated herein by reference.

FIELD OF THE INVENTION

The present invention relates to water-soluble selective auxin-type herbicides and methods for controlling unwanted vegetation.

BACKGROUND OF THE INVENTION

The control of unwanted vegetation is a continually important effort as it is needed for reducing health problems, such as allergies, the removal of poisonous/noxious weeds, increasing crop productivity, as well as improving the general aesthetics around the home. Unwanted vegetation can be controlled using herbicides that are either selective or non-selective. An example of a commonly used non-selective herbicide is glyphosate, marketed under the trade name Roundup®, among others, which kills all vegetation it contacts. Alternatively, a selective herbicide only affects the undesired plant species while leaving the desired species relatively unaffected. An example of a well-known auxin-type selective herbicide is 2,4-dichlorophenoxyacetic acid (also known as "2,4-D"), which is commonly used for the removal of broadleaf weeds growing in grass and turf.

There are a variety of selective herbicides that are available on the market for the selective control of grass and broadleaf weeds growing in a variety of crops. The majority of these herbicides are synthetic compounds, with some herbicides raising concerns in recent years as to their safety to humans and the environment in general. Within the context of postemergent broadleaf weed control in grass, auxin-type herbicides are commonly used. There are four main families of synthetic auxin-type herbicides available on the market, including: the phenoxyacetic acid or phenoxyalkanoic acid family (e.g. 2,4-D), the benzoic acid family (e.g. dicamba), the pyridine carboxylic acid or picolinic acid family (e.g. triclopyr), and the quinolinecarboxylic acid family (e.g. quinclorac). These auxin-type herbicides are systemic compounds that have activity against a number of broadleaf weeds including perennial species. A number of registered products exist with these compounds, some using the individual compounds alone while others have two or three combined together (e.g., Killex® contains 2,4-D, mecoprop and dicamba).

A drawback of the synthetic auxin-type herbicides is their slow speed of activity. Often herbicidal activity is not seen for several weeks after application. Moreover, the products that are available for use by homeowners often do not result in adequate weed control with one application, resulting in the need for additional applications in order to achieve acceptable weed control.

Accordingly, there is a need in the art for novel methods and compositions for the improvement and enhancement of selective auxin-type herbicides that will benefit both consumers and the environment.

SUMMARY OF THE INVENTION

The present invention is generally directed to methods and compositions for an enhanced water-soluble selective herbicide. In particular, the present invention provides an enhanced and/or synergistic, effective, fast-acting, long-lasting water-soluble selective herbicide that will remove unwanted broadleaf weeds from grass and turf. In one embodiment, an exemplary method for treating undesired vegetation can include providing a selective herbicidal composition that includes a water-soluble selective auxin-type herbicide and a chelating agent complexed with at least one transition metal, and contacting vegetation with a herbicidally effective amount of the composition such that unwanted vegetation is controlled, while desired vegetation is unaffected.

In one aspect, the exemplary method can provide a selective herbicidal composition that includes a water-soluble selective auxin-type herbicide in the form of an acid, an ester, a salt, and combinations thereof. The metal component of the composition can be a transition metal selected from the group consisting of copper, iron, manganese, zinc, and combinations thereof. The chelating agent component of the composition can be a chelating agent selected from the group consisting of an aminopolycarboxylate, an amino acid, a salicylate, and combinations thereof.

In another embodiment, an exemplary method for treating undesired vegetation involves providing a herbicidal composition that can include a water-soluble selective auxin-type herbicide and an ethylenediaminedisuccinic compound, and contacting vegetation with a herbicidally effective amount of the composition such that unwanted vegetation is selectively controlled, while desired vegetation is undamaged.

In one aspect, the exemplary method can provide a herbicidal composition wherein a ethylenediaminedisuccinic compound is in the form of an acid or a salt. When the ethylenediaminedisuccinic compound is a salt, it is selected from the group consisting of sodium salts, potassium salts, ammonium salts, and combinations thereof.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides a more environmentally compatible selective herbicide that is effective to remove unwanted broadleaf weeds while leaving grasses and other desirable plants unaffected. The composition comprises a water-soluble auxin-type herbicide and a chelating agent that is complexed with at least one transition metal. The composition is useful in a method of treating undesired vegetation in which the composition is provided and vegetation is contacted with a herbicidally effective amount of the composition such that unwanted vegetation is controlled, while desired vegetation is unaffected. The sources of the chelating agent and the transition metal that form the complex can vary, as described below. In another embodiment, the composition used to selectively kill unwanted vegetation is an environmentally compatible selective herbicide composition comprising the combination of a water-soluble selective auxin-type herbicide and an ethylenediaminedisuccinic compound. One characteristic of the compositions and the methods disclosed herein is the enhanced and/or synergistic activity that is achieved when the composition is applied to vegetation to control undesired vegetation.

In one aspect, the metal component used to form the complex of the present invention includes a transition metal. Suitable transition metal ions include, for example, copper ions, iron ions, manganese ions, zinc ions, and combinations thereof. In an exemplary embodiment, the metal component includes an iron ion, which can be present in a variety of ionic states. By way of non-limiting example, iron ions used in the present invention can be added as $Fe^{+2}$ ions, $Fe^{+3}$ ions, and mixtures thereof.

The metal component of the present invention can be added in a variety of forms. In one embodiment, the metal ions can be added as a metal salt. Exemplary metal salts include metal chlorides, metal sulfates, metal nitrates, metal citrates, metal phosphates, metal sulfides, metal sulfites, metal succinates, metal gluconates, metal lactates, metal formates, metal nitrites, metal salicylates, metal carboxylic acids, and combinations thereof.

Another component of the herbicidal composition that forms a complex with a transition metal is a chelating agent. A variety of chelating agents can be used in the water-soluble selective auxin-type herbicide compositions of the present invention to form a metal chelate. By way of non-limiting example, suitable chelating agents include aconitic acid, alanine diacetic acid (ADA), alkoyl ethylene diamine triacetic acids (e.g., lauroyl ethylene diamine triacetic acids (LED3A)), aminotri (methylenephosphonic acid) (ATMP), asparticaciddiacetic acid (ASDA), asparticacidmonoacetic acid, diamino cyclohexane tetraacetic acid (CDTA), citraconic acid, citric acid, 1,2-diaminopropanetetraacetic acid (DPTA-OH), 1,3-diamino-2-propanoltetraacetic acid (DTPA), diethanolamine, diethanol glycine (DEG), diethylenetriaminepentaacetic acid (DTPA), diethylene triamine pentamethylene phosphonic acid (DTPMP), diglycolic acid, dipicolinic acid (DPA), ethanolaminediacetic acid, ethanoldiglycine (EDG), ethionine, ethylenediamine (EDA), ethylenediaminediglutaric acid (EDDG), ethylenediamineddi(hydroxyphenylacetic acid (EDDHA), ethylenediaminedipropionic acid (EDDP), ethylenediaminedisuccinate (EDDS), ethylenediaminemonosuccinic acid (EDMS), ethylenediaminetetraacetic acid (EDTA), ethylenediaminetetrapropionic acid (EDTP), ethyleneglycolaminoethylestertetraacetic acid (EGTA), gallic acid, glucoheptonic acid, gluconic acid, glutamicaciddiacetic acid (GLDA), glutaric acid, glyceryliminodiacetic acid, glycinamidedisuccinic acid (GADS), glycoletherdiaminetetraacetic acid (GEDTA), 2-hydroxyethyldiacetic acid, hydroxyethylenediaminetriacetic acid (HEDTA), hydroxyethyldiphosphonic acid (HEDP), 2-hydroxyethyl imino diacetic acid (HIMDA), hydroxyiminodiacetic acid (HIDA), 2-hydroxy propylene diamine disuccinic acid (HPDDS), iminodiacetic acid (IDA), iminodisuccinic acid (IDS), itaconic acid, lauroyl ethylene diamine triacetic acids (LED3A), malic acid, malonic acid, methylglycinediacetate (MGDA), methyliminodiacetic acid (MIDA), monoethanolamine, nitrilotripropionic acid (NPA), N-phosphonomethyl glycine (glyphosate), propyldiamine tetraacetic acid (PDTA), salicylic acid, serinediacetic acid (SDA), sorbic acid, succinic acid, sugars, tartaric acid, tartronic acid, triethanolamine, triethylenetetraamine, triethylene tetraamine hexaacetic acid (TTHA), and combinations thereof. In an exemplary embodiment, the chelating agent is HEDTA, EDTA, CDTA, EDDS, GLDA MGDA, IDS, EDG, DTPA, isomers thereof, and combinations thereof.

Other suitable chelating agents that can be used in the herbicidal compositions of the present invention to form the metal chelate include citric acid, salicylic acid and salts thereof, such as ammonium salicylate, and combinations thereof. Amino acids can also be used as chelating agents in the present invention. Suitable amino acids include alanine, arginine, asparagine, aspartic acid, glutamic acid, glutamine, glycine, histidine, isoleucine, leucine, lysine, methionine, proline, serine, threonine, tyrosine, valine, and combinations thereof.

The chelating agent can be present in the herbicidal composition in a variety of forms, alone or in combination. In one embodiment, the chelating agent can be in the form of a free acid. In another embodiment the chelating agent can be a salt. Exemplary salt forms of the chelating agent include sodium salts, potassium salts, calcium salts, ammonium salts, amine salts, amide salts, magnesium salts, and combinations thereof. The actual compounds that can be used to form this component of the herbicidal composition include those chelating agents described above.

Suitable water-soluble selective auxin-type herbicides for use with this invention include aminopyralid (4-amino-3,6-dichloropyridine-2-carboxylic acid), clomeprop ((RS)-2-(2,4-dichloro-m-tolyloxy)propionanilide), clopyralid (3,6-dichloro-2-pyridinecarboxylic acid), 2,4-D ((2,4-dichlorophenoxy)acetic acid), dicamba (3,6-dichloro-2-methoxybenzoic acid), dichlorprop ((±)-2-(2,4-dichlorophenoxy)propanoic acid), fluroxypyr ([(4-amino-3,5-dichloro-6-fluoro-2-pyridinyl)oxy]acetic acid), MCPA ((4-chloro-2-methylphenoxy)acetic acid), mecoprop ((±)-2-(4-chloro-2-methylphenoxy)propanoic acid), picloram (4-amino-3,5,6-trichloro-2-pyridinecarboxylic acid), quinclorac (3,7-dichloro-8-quinolinecarboxylic acid), quinmerac (7-chloro-3-methyl-8-quinolinecarboxylic acid), triclopyr ([(3,5,6-trichloro-2-pyridinyl)oxy]acetic acid), their salts, acids, esters, and combinations thereof.

Some of the water-soluble selective auxin-type herbicide components of the present invention can also be added in a variety of forms. In one embodiment, the auxin-type herbicide can be added as a salt, and exemplary salts include potassium salts, sodium salts, ammonium salts, isopropylamine salts, dimethylamine salts, triethylamine salts, diglycolamine salts, triisopropanolamine salts, triisopropanolammonium salts, monoethanolamine salts, diethanolamine salts, and combinations thereof. In another embodiment, the herbicide can be added as an acid. In yet another embodiment, the herbicide can be added as an ester such as a butoxyethyl ester, ethylhexyl ester, isooctyl ester, methylheptyl ester, and combinations thereof.

Where the herbicide composition includes a metal salt, a chelating agent, and a water-soluble selective auxin-type herbicide, the concentration of the metal ion, the chelating agent and the herbicide can vary significantly. By way of non-limiting example, the concentration of metal ions applied to the plant should be in the range of about 0.01 to 5% by weight, and more preferably in the range of about 0.05 to 2% by weight; the concentration of the chelating agent applied to the plant can be in the range of about 0.1 to 25% by weight, and more preferably in the range of about 0.2 to 10% by weight, the concentration of the water-soluble selective auxin-type herbicide applied to the plant can be in the range of about 0.00001 to 20% by weight, and more preferably in the range of about 0.00005 to 15% by weight.

In another aspect, the composition comprises a water-soluble selective auxin-type herbicide and an ethylenediaminedisuccinic compound. The ethylenediaminedisuccinic compound can be in the form of an acid or a salt. Exemplary salt forms of this compound include sodium salts, potassium salts, ammonium salts, and combinations thereof. In this embodiment, the sodium, potassium or ammonium ions can be present in the composition at a concentration in the range of about 0.01 to 5% by weight, and more preferably at a concentration in the range of about 0.05 to 2% by weight, while the ethylenediaminedisuccinic compound can be present in the composition at a concentration in the range of about 0.1 to 25% by weight, and more preferably at a concentration in the range of about 0.2 to 10 % by weight, when the composition is applied to vegetation. The concentration of the water-soluble selective auxin-type herbicide applied to the plant can be in the range of about 0.00001 to 20% by weight, and more preferably at a concentration in the range of about 0.00005 to 15% by weight.

Besides the ingredients described above, a variety of other components can be added to the herbicide compositions. By way of non-limiting example, these additives can include fertilizers, growth regulators, selective herbicides, thickening agents, dyes, and combinations thereof.

A variety of fertilizers may be added to the herbicidal composition of the present invention. The end-use concentration of added fertilizer(s) can vary, but preferably, the concentration of fertilizer is in the range of about 0.1 to 5% by weight.

A variety of growth regulators may also be added to the herbicidal composition of the present invention. By way of non-limiting example, the growth regulators added to the herbicidal compositions can include maleic hydrazide (MH), cycocel (2-chloroethyl-trimethyl ammonium chloride), and combinations thereof. The end-use concentration of the additional growth regulators can vary, but preferably, the concentration is between about 0.01 and 2% by weight.

The herbicidal compositions of the present invention can also include natural growth regulators, such as ammonium salicylate, jasmonates, ethylene, auxins, gibberellins, cytokinins, abscisic acid, and combinations thereof. The end-use concentration of these natural growth regulators can vary, but preferably, the concentration is in the range of about 0.001 to 5% by weight.

Furthermore, a variety of thickening agents may be added to the herbicidal compositions disclosed herein. Exemplary thickening agents include Rhodopol 23 (Rhodia), VanGel B (R. T. Vanderbilt), Kelzan S (C.P. Kelco), guar gum, propylene glycol, glycerol, and combinations thereof. The end-use concentration of added thickening agent(s) can vary, but preferably, the concentration is in the range of about 0.01 to 1% by weight.

Other additives may be included in the herbicidal compositions disclosed herein as well. By way of non-limiting example, such other additives can include humectants, antioxidants, stabilizing agents, wetting agents, surfactants, herbicide synergists, solvents, sequestrants, and combinations thereof. Suitable humectants include, for example, propylene glycol, glycerin, beet molasses, and combinations thereof. Suitable antioxidants include, for example, citric acid, while suitable stabilizing agents include citric acid, ammonium salts, and combinations thereof. Suitable wetting agents include, for example, carboxylic acids and the salts thereof and silicone polymers such as Silwet 77 (G.E. Co. Advanced Materials Silicones). The end-use concentration of these additives may vary, but preferably, the concentration is in the range of about 0.01 to 5% by weight.

In use, the formulation of the water-soluble selective auxin-type herbicide of the present invention can vary. Preferably, the herbicidal compositions are formed as a ready-to-use composition, a liquid concentrate, a tank-mix, or a dry concentrate. The solvents used in the ready-to-use liquid composition and liquid concentrate forms can also vary and exemplary solvents include propylene glycol, glycerin, alcohols such as tetrahydrofurfuryl alcohol (THFA), and combinations thereof.

The pH of the herbicidal solution can vary, but the herbicidal compositions of the present invention are effective over a wide range of pH values. An exemplary pH is in the range of about 1.5 to 10. After the formulation has been prepared, the pH of the solution can be measured and adjusted as necessary. The pH values can be measured using standard pH meters, with glass bulb electrodes.

An exemplary ready-to-use (RTU) formulation according to one embodiment of the present invention includes FeHEDTA metal chelate with 0.4% iron and 0.6% Killex®. The ingredients used to form this composition are as follows:

| Ingredient | Concentration by weight (%) |
| --- | --- |
| Deionized water | 95.4% |
| Na$_3$HEDTA | 2.8% |
| FeCl$_3$ | 1.2% |
| Killex ®* | 0.6% |

*Killex ® contains 2,4-D (9.5%), mecoprop (5%) and dicamba (0.9%).

The RTU formulation shown above is prepared by adding deionized water to a vessel, and adding ferric chloride to the water while stirring. Once dissolved, the Na$_3$HEDTA is added, followed by additional stirring to dissolve the Na$_3$HEDTA. The pH is then adjusted to between 6 and 8. Lastly, Killex® is added, followed by additional stirring until thoroughly mixed. This solution can then be sprayed onto areas of lawn and weeds using a handheld trigger sprayer, a pump-wand sprayer, or broadcast sprayer, at a rate of about 200 ml/m$^2$.

The herbicide compositions of the present invention can be applied to a variety of undesired vegetation in both residential and commercial plant or crop areas. Preferably, the herbicide compositions are effective to selectively control broadleaf weeds growing in grass and turf areas. The herbicidal compositions disclosed herein are very effective against numerous common broadleaf weeds, mosses, liverworts, and algae. Grass and turf areas that are infested with undesired vegetation can be entirely sprayed with a herbicidal composition of the present invention to selectively remove the unwanted vegetation, while leaving the grass, turf and other desired plants undamaged.

One advantageous characteristic of the herbicidal compositions of the present invention is their relatively fast-acting nature. The herbicidal compositions described in this invention show signs of herbicidal activity within days compared to the weeks typically required for known auxin-type herbicides to achieve the same level of activity. In addition, an enhanced and/or synergistic level of herbicidal activity is obtained against the unwanted vegetation with the herbicidal compositions of the current invention, relative to the individual components if used alone. This improvement in herbicidal activity can be seen within days of treatment, lasting up to many weeks after treatment. Furthermore, the improved weed activity that results from the herbicide compositions of the current invention also allows for a reduction in the amount of the auxin-type herbicide that is required to achieve comparable weed control to the full rate of the auxin-type herbicide on its own. Reducing auxin-type herbicide rates while maintaining similar weed control is beneficial for consumers and the environment in general, particularly since some of these auxin-type herbicides have raised health concerns in recent years. Although increased broadleaf weed activity results with the herbicide compositions of the present invention, selectivity is maintained wherein treated grass species remain relatively unaffected, sometimes with less injury seen than when the individual components are applied on their own.

The following non-limiting examples serve to further describe the invention. For the greenhouse tests, plants were grown in a commercial greenhouse mix, using supplemental lighting and heating. Plants were fertilized with an all purpose water-soluble fertilizer mix of 20-20-20 (N-P-K; Plant-Prod®) as needed. All broadleaf weeds were grown individually in a 2¼-inch pot until they were a suitable size for herbicide tests (actual weed size is reported in examples below). Perennial ryegrass was also grown in 2¼-inch pots, however many grass seeds were sown in the pot to simulate a small section of turf. Grass plants were continually trimmed to a height of 4 cm, simulating that of a homeowner's lawn. For field tests, plots ¼ in$^2$ in size were marked out in areas containing the targeted broadleaf weed species growing in turf grass. Plots were continually mowed to simulate a homeowner's lawn. All of the tested herbicidal solutions were sprayed onto the plants at a rate of 200 ml/m$^2$. In all of the examples, the amounts of the various herbicide components are identified as a percent on a weight basis.

Killex® (Scotts Canada, Ltd., Ontario, Canada) is a commonly used selective lawn herbicide and was used as the commercial herbicide for herbicide combinations. The labeled dilution and application rates for Killex® are 6 ml into 1 L of solution (0.6%) applied at 200 ml/m$^2$.

All visual plant damage assessments were made using a quantitative rating scale; percent control relative to the untreated check (0=no effect; 100=plant death).

EXAMPLE 1

Objective: To evaluate the combination of various iron chelates with Killex® for herbicidal activity and grass injury.

Materials and Methods: This trial was conducted in the greenhouse. Nine pots of white clover and 10 pots of perennial ryegrass were selected for each treatment. Herbicidal solutions were prepared using deionized water. The treatments were applied using a handheld trigger sprayer at 200 ml/m$^2$. All treatments were applied once. Phytotoxicity (%) was assessed 4, 7, and 14 days after application (A4, A7, and A14).

TABLE 1

Plant stages at the commencement of this study.

| | White clover | Perennial ryegrass |
|---|---|---|
| Leaf # | 20+ | — |
| Plant Height (cm) | 17-20 | 4 |
| Growth Stage | flower | vegetative |

TABLE 2

Phytotoxicity (%) against white clover.

| | Phytotoxicity (%) | | |
|---|---|---|---|
| White Clover | A4 | A7 | A14 |
| Control | 0 | 0 | 0 |
| FeMGDA 0.4% Fe | 4 | 5 | 2 |
| FeIDS 0.4% Fe | 7 | 10 | 13 |
| FeEDTA 0.4% Fe | 15 | 15 | 6 |
| FeHEDTA 0.4% Fe | 22 | 19 | 15 |
| Killex ® 0.6% | 10 | 11 | 28 |
| FeMGDA 0.4% Fe + Killex ® 0.6% | 18 | 20 | 38 |
| FeIDS 0.4% Fe + Killex ® 0.6% | 36 | 37 | 53 |
| FeEDTA 0.4% Fe + Killex ® 0.6% | 27 | 37 | 39 |
| FeHEDTA 0.4% Fe + Killex ® 0.6% | 57 | 66 | 66 |

TABLE 3

Phytotoxicity (%) against perennial ryegrass.

| | Phytotoxcity (%) | | |
|---|---|---|---|
| Perennial ryegrass | A4 | A7 | A14 |
| Control | 0 | 0 | 0 |
| FeMGDA 0.4% Fe | 0 | 0 | 0 |
| FeIDS 0.4% Fe | 6 | 5 | 0 |
| FeEDTA 0.4% Fe | 4 | 2 | 0 |
| FeHEDTA 0.4% Fe | 8 | 7 | 1 |
| Killex ® 0.6% | 1 | 1 | 0 |
| FeMGDA 0.4% Fe + Killex ® 0.6% | 7 | 5 | 0 |
| FeIDS 0.4% Fe + Killex ® 0.6% | 7 | 5 | 1 |
| FeEDTA 0.4% Fe + Killex ® 0.6% | 4 | 2 | 0 |
| FeHEDTA 0.4% Fe + Killex ® 0.6% | 5 | 4 | 3 |

EXAMPLE 2

Objective: To evaluate the combination of FeHEDTA metal chelates with Killex® for herbicidal activity and grass injury.

Materials and Methods: This trial was conducted in the greenhouse. Nine pots of white clover and 10 pots of perennial ryegrass were selected for each treatment. Herbicide solutions were prepared using deionized water. The treatments were applied using a hand-trigger sprayer at 200 ml/m$^2$. All treatments were applied once. Phytotoxicity (%) was assessed 4, 7, and 14 days after application (A4, A7, and A14).

TABLE 4

Plant stages at the commencement of this study.

| | White clover | Perennial ryegrass |
|---|---|---|
| Leaf # | 20+ | — |
| Plant Height (cm) | 15-19 | 4 |
| Growth Stage | vegetative | vegetative |

TABLE 5

Phytotoxicity (%) against white clover.

| | Phytotoxicity (%) | | |
|---|---|---|---|
| White Clover | A4 | A7 | A14 |
| Control | 0 | 0 | 0 |
| FeHEDTA 0.4% Fe | 27 | 50 | 18 |

TABLE 5-continued

Phytotoxicity (%) against white clover.

| White Clover | Phytotoxicity (%) | | |
|---|---|---|---|
| | A4 | A7 | A14 |
| Killex ® 0.6% | 11 | 12 | 28 |
| FeHEDTA 0.4% Fe + Killex ® 0.6% | 58 | 71 | 73 |

TABLE 6

Phytotoxicity (%) on perennial ryegrass.

| Perennial ryegrass | Phytotoxicity (%) | | |
|---|---|---|---|
| | A4 | A7 | A14 |
| Control | 0 | 0 | 0 |
| FeHEDTA 0.4% Fe | 2 | 1 | 2 |
| Killex ® 0.6% | 0 | 0 | 0 |
| FeHEDTA 0.4% Fe + Killex ® 0.6% | 1 | 1 | 1 |

EXAMPLE 3

Objective: To evaluate the combination of FeHEDTA metal chelate with Killex® at reduced rates.

Materials and Methods: This trial was conducted in the greenhouse. Ten broadleaf plantain plants and 5 pots of perennial ryegrass were selected for each treatment. Herbicide solutions were prepared using deionized water. The treatments were applied using a hand-trigger sprayer at 200 ml/m². All treatments were applied once. Phytotoxicity (%) was assessed 7 days after application (A7).

TABLE 7

Plant stages at the commencement of this study.

| | Broadleaf plantain | Perennial ryegrass |
|---|---|---|
| Leaf # | 4-7 | — |
| Plant Diameter (cm) | 25-45 | 3-5 (height) |
| Growth Stage | vegetative | vegetative |

TABLE 8

Phytotoxicity (%) against broadleaf plantain.

| Broadleaf plantain | A7 Phytotoxicity (%) | | | |
|---|---|---|---|---|
| | Killex ® 0% | Killex ® 0.15% | Killex ® 0.3% | Killex ® 0.6% |
| FeHEDTA 0% Fe | 0 | 14 | 23 | 24 |
| FeHEDTA 0.1% Fe | 9 | 25 | 29 | 36 |
| FeHEDTA 0.2% Fe | 10 | 27 | 30 | 43 |
| FeHEDTA 0.4% Fe | 22 | 35 | 42 | 53 |

TABLE 9

Phytotoxicity (%) against perennial ryegrass.

| Perennial ryegrass | A7 Phytotoxicity (%) | | | |
|---|---|---|---|---|
| | Killex ® 0% | Killex ® 0.15% | Killex ® 0.3% | Killex ® 0.6% |
| FeHEDTA 0% Fe | 0 | 1 | 1 | 1 |
| FeHEDTA 0.1% Fe | 1 | 1 | 3 | 2 |

TABLE 9-continued

Phytotoxicity (%) against perennial ryegrass.

| Perennial ryegrass | A7 Phytotoxicity (%) | | | |
|---|---|---|---|---|
| | Killex ® 0% | Killex ® 0.15% | Killex ® 0.3% | Killex ® 0.6% |
| FeHEDTA 0.2% Fe | 1 | 1 | 2 | 1 |
| FeHEDTA 0.4% Fe | 2 | 1 | 1 | 1 |

EXAMPLE 4

Objective: To evaluate the combination of $NH_4$-, Na-, K- and Fe-EDDS with Killex® for herbicidal activity and grass injury.

Materials and Methods: This trial was conducted in the greenhouse. Ten broadleaf plantain plants and 10 pots of perennial ryegrass were selected for each treatment. Herbicide solutions were prepared using deionized water. The treatments were applied using a hand-trigger sprayer at 200 m/m². All treatments were applied once. Phytotoxicity (%) was assessed 21 days after application (A21).

TABLE 10

Plant stages at the commencement of this study.

| | Broadleaf plantain | Perennial ryegrass |
|---|---|---|
| Leaf # | 12-18 | — |
| Plant Diameter (cm) | 40-50 | 4-5 (height) |
| Growth Stage | flower | vegetative |

TABLE 11

Phytotoxicity (%) against broadleaf plantain.

| Broadleaf plantain | Phytotoxicity (%) A21 |
|---|---|
| Control | 0 |
| $NH_4$EDDS 2.09% a.e.[a] | 0 |
| NaEDDS 2.09% a.e. | 6 |
| KEDDS 2.09% a.e. | 6 |
| FeEDDS 0.4% Fe | 2 |
| Killex ® 0.6% | 29 |
| $NH_4$EDDS 2.09% a.e. + Killex ® 0.6% | 43 |
| NaEDDS 2.09% a.e. + Killex ® 0.6% | 59 |
| KEDDS 2.09% a.e. + Killex ® 0.6% | 54 |
| FeEDDS 0.4% Fe + Killex ® 0.6% | 47 |

[a] abbreviation a.e. = acid equivalent

TABLE 12

Phytotoxicity (%) on LOLPE.

| LOLPE | Phytotoxicity (%) A21 |
|---|---|
| Control | 0 |
| $NH_4$EDDS 2.09% a.e.[a] | 0 |
| NaEDDS 2.09% a.e. | 0 |
| KEDDS 2.09% a.e. | 0 |
| FeEDDS 0.4% Fe | 0 |
| Killex ® 0.6% | 0 |
| $NH_4$EDDS 2.09% a.e. + Killex ® 0.6% | 0 |
| NaEDDS 2.09% a.e. + Killex ® 0.6% | 0 |
| KEDDS 2.09% a.e. + Killex ® 0.6% | 0 |
| FeEDDS 0.4% Fe + Killex ® 0.6% | 0 |

[a] abbreviation a.e. = acid equivalent

EXAMPLE 5

Objective: To evaluate the combination of various Fe chelates with Killex® for herbicidal activity and grass injury.

Materials and Methods: This trial was conducted in the greenhouse. Seven dandelion plants and 10 pots of perennial ryegrass were selected for each treatment. Herbicide solutions were prepared using deionized water. The treatments were applied using a hand-trigger sprayer at 200 ml/m$^2$. All treatments were applied once. Phytotoxicity (%) was assessed 29 days after treatment (A29).

TABLE 13

Plant stages at the commencement of this study.

| | Dandelion | Perennial ryegrass |
|---|---|---|
| Leaf # | 15-34 | — |
| Plant Diameter (cm) | 25-30 | 3-4 (height) |
| Growth Stage | flower | vegetative |

TABLE 14

Phytotoxicity (%) against dandelion.

| Dandelion | Phytotoxicity (%) A29 |
|---|---|
| Control | 0 |
| FeMGDA 0.4% Fe | 12 |
| FeIDS 0.4% Fe | 28 |
| FeHEDTA 0.4% Fe | 24 |
| Killex ® 0.6% | 54 |
| FeMGDA 0.4% Fe + Killex ® 0.6% | 79 |
| FeIDS 0.4% Fe + Killex ® 0.6% | 98 |
| FeHEDTA 0.4% Fe + Killex ® 0.6% | 92 |

TABLE 15

Phytotoxicity (%) on Perennial ryegrass.

| Perennial Ryegrass | Phytotoxicity (%) A29 |
|---|---|
| Control | 0 |
| FeMGDA 0.4% Fe | 0 |
| FeIDS 0.4% Fe | 0 |
| FeHEDTA 0.4% Fe | 0 |
| Killex ® 0.6% | 0 |
| FeMGDA 0.4% Fe + Killex ® 0.6% | 0 |
| FeIDS 0.4% Fe + Killex ® 0.6% | 0 |
| FeHEDTA 0.4% Fe + Killex ® 0.6% | 0 |

EXAMPLE 6

Objective: To evaluate the combination of FeIDS and/or FeHEDTA metal chelates with Killex®.

Materials and Methods: Plots ¼ m$^2$ in size were marked out in white clover and Park Lawn (turfgrass mixture comprising of 65% perennial ryegrass, 25% chewings/creeping red fescue and 10% Kentucky bluegrass) area in the field. Herbicide solutions were prepared using deionized water. All treatments were replicated twice. The treatments were applied using a hand trigger sprayer at 200 ml/m$^2$. All treatments were applied once. Phytotoxicity (%) was assessed on 7 days after treatment (A7).

TABLE 16

Plant stages at the commencement of this study.

| | White clover | Park Lawn |
|---|---|---|
| Leaf # | 20+ | — |
| Plant Height (cm) | 3-12 | 3-11 |
| Growth Stage | vegetative | vegetative |
| Coverage (%) | 68 | 33 |

TABLE 17

Phytotoxicity (%) against white clover.

| White clover | Phytotoxicity (%) A7 |
|---|---|
| Control | 0 |
| FeIDS 0.4% Fe | 15 |
| FeHEDTA 0.4% Fe | 48 |
| FeIDS 0.2% Fe + FeHEDTA 0.2% Fe | 38 |
| Killex ® 0.6% | 23 |
| FeIDS 0.4% Fe + Killex ® 0.6% | 69 |
| FeHEDTA 0.4% Fe + Killex ® 0.6% | 91 |
| FeIDS 0.2% Fe + FeHEDTA 0.2% Fe + Killex ® 0.6% | 85 |

TABLE 18

Phytotoxicity (%) on Park Lawn.

| Park Lawn | Phytotoxicity (%) A7 |
|---|---|
| Control | 0 |
| FeIDS 0.4% Fe | 0 |
| FeHEDTA 0.4% Fe | 3 |
| FeIDS 0.2% Fe + FeHEDTA 0.2% Fe | 1 |
| Killex ® 0.6% | 0 |
| FeIDS 0.4% Fe + Killex ® 0.6% | 0 |
| FeHEDTA 0.4% Fe + Killex ® 0.6% | 2 |
| FeIDS 0.2% Fe + FeHEDTA 0.2% Fe + Killex ® 0.6% | 0 |

EXAMPLE 7

Objective: To evaluate the combination of Cu-, Mn- or ZnHEDTA metal chelates with Killex®.

Materials and Methods: This trial was conducted in the greenhouse. Ten white clover plants and 10 pots of perennial ryegrass were selected for each treatment. Herbicide solutions were prepared using deionized water. The treatments were applied using a hand-trigger sprayer at 200 ml/m$^2$. All treatments were applied once. Phytotoxicity (%) was assessed 4 and 7 days after treatment (A4 and A7).

TABLE 19

Plant stages at the commencement of this study.

| | White clover | Perennial ryegrass |
|---|---|---|
| Leaf # | 20+ | — |
| Plant Height (cm) | 3-16 | 2 |
| Growth Stage | veg | veg |

TABLE 20

Phytotoxicity (%) against white clover.

| White clover | Phytotoxicity (%) | |
|---|---|---|
| | A4 | A7 |
| Control | 0 | 0 |
| CuHEDTA 0.4% Cu | 32 | 62 |
| MnHEDTA 0.4% Mn | 9 | 12 |
| ZnHEDTA 0.4% Zn | 4 | 3 |
| Killex 0.6% | 18 | 23 |
| CuHEDTA 0.4% Cu + Killex 0.6% | 46 | 69 |
| MnHEDTA 0.4% Mn + Killex 0.6% | 33 | 49 |
| ZnHEDTA 0.4% Zn + Killex 0.6% | 36 | 44 |

TABLE 21

Phytotoxicity (%) on perennial ryegrass.

| Perennial ryegrass | Phytotoxicity (%) | |
|---|---|---|
| | A4 | A7 |
| Control | 0 | 0 |
| CuHEDTA 0.4% Cu | 3 | 3 |
| MnHEDTA 0.4% Mn | 1 | 1 |
| ZnHEDTA 0.4% Zn | 1 | 0 |
| Killex 0.6% | 1 | 1 |
| CuHEDTA 0.4% Cu + Killex 0.6% | 3 | 2 |
| MnHEDTA 0.4% Mn + Killex 0.6% | 2 | 3 |
| ZnHEDTA 0.4% Zn + Killex 0.6% | 2 | 2 |

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating undesired vegetation, comprising the steps of:
providing a selective herbicidal composition comprising a water-soluble selective auxin-type herbicide selected from the group consisting of phenoxyacetic acid, phenoxyalkanoic acid, benzoic acid and mixtures thereof, and a chelating agent complexed with at least one transition metal; and contacting vegetation with a herbicidally effective amount of the composition such that unwanted vegetation is controlled, while desired vegetation is unaffected.

2. The method of claim 1, wherein the water-soluble selective auxin-type herbicide is selected from the group consisting of (2,4-dichlorophenoxy)acetic acid, 3,6-dichloro-2-methoxybenzoic acid, (+)-2-(2,4-dichlorophenoxy)propanoic acid, (4-chloro-2-methylphenoxy)acetic acid, (+)-2-(4-chloro-2-methylphenoxy)propanoic acid, and combinations thereof.

3. The method of claim 2 wherein the water-soluble selective auxin-type herbicide is in the form of an acid, an ester, a salt, and combination thereof.

4. The method of claim 1, wherein the water-soluble selective auxin-type herbicide is present within the composition at a concentration in a range of about 0.00001 to 20% by weight when the composition is applied to the vegetation.

5. The method of claim 1, wherein the transition metal is selected from the group consisting of copper, iron, manganese, zinc, and combinations thereof.

6. The method of claim 5, wherein the transition metal is iron.

7. The method of claim 1, wherein the transition metal is present in the composition at a concentration in a range of about 0.01 to 5% by weight when the composition is applied to the vegetation.

8. The method of claim 1, wherein the chelating agent is selected from the group consisting of an aminopolycarboxylate, an amino acid, a salicylate, and combinations thereof.

9. The method of claim 8, wherein the aminopolycarboxylate is selected from the group consisting of ethylenediaminedisuccinic acid, ethylenediaminetetraacetic acid, ethanoldiglycine, hydroxyethylenediaminetriacetic acid, methylglycinediacetic acid, glutamicaciddiacetic acid, trans-1,2-diaminocyclohexane-N,N,N',N'tetraacetic acid, diethylenetriaminepentaacetic acid, iminodisuccinic acid, their salts, and combinations thereof.

10. The method of claim 1, wherein the chelating agent is present within the composition at a concentration in a range of about 0.1 to 25% by weight when the composition is applied to the vegetation.

11. The method of claim 1, further comprising an additional component selected from the group consisting of growth regulators, fertilizers, selective herbicides, thickening agents, humectants, antioxidants, surfactants, stabilizing agents, wetting agents, sequestrants, solvents, dyes, and combinations thereof.

12. A method of treating undesired vegetation, comprising:
providing a herbicidal composition comprising a water-soluble selective auxin-type herbicide selected from the group consisting of phenoxyacetic acid, phenoxyalkanoic acid, benzoic acid and mixtures thereof, and an ethylenediaminedisuccinic compound; and
contacting vegetation with a herbicidally effective amount of the composition such that unwanted vegetation is selectively controlled, while desired vegetation is undamaged.

13. The method of claim 12, wherein the ethylenediaminedisuccinic compound is in the form of an acid or a salt.

14. The method of claim 13, wherein the ethylenediaminedisuccinic salt is selected from the group consisting of sodium salts, potassium salts, ammonium salts, and combinations thereof.

15. The method of claim 14, wherein a sodium ion, potassium ion or ammonium ion component of the ethylenediaminedisuccinic salt is present within the composition in a range of about 0.01 to 5% by weight when the composition is applied to the vegetation.

16. The method of claim 13, wherein the ethylenediaminedisuccinic compound of the ethylenediaminedisuccinic salt is present within the composition at a concentration in a range of about 0.1 to 25% by weight when the composition is applied to the vegetation.

17. The method of claim 12, further comprising an additional component selected from the group consisting of growth regulators, fertilizers, selective herbicides, thickening agents, humectants, antioxidants, surfactants, stabilizing agents, wetting agents, sequestrants, solvents, dyes and combinations thereof.

18. A method for treating undesired vegetation, comprising the steps of:
providing a selective herbicidal composition comprising a water-soluble selective auxin-type herbicide selected from the group consisting of phenoxyacetic acid, phenoxyalkanoic acid, benzoic acid and mixtures thereof, a chelating agent and a metal salt; and contacting vegetation with a herbicidally effective amount of the composition such that unwanted vegetation is controlled, while desired vegetation is unaffected.

19. The method of claim 18, wherein a metal component of the metal salt is a transition metal.

* * * * *